(12) United States Patent
Odell

(10) Patent No.: US 6,508,181 B1
(45) Date of Patent: Jan. 21, 2003

(54) IMAGING TABLE MOUNT

(75) Inventor: Robert W. Odell, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/687,996

(22) Filed: Oct. 13, 2000

(51) Int. Cl.⁷ ............................................... A47B 23/00

(52) U.S. Cl. ........................................ 108/49; 108/102

(58) Field of Search ............................ 108/49, 93, 94, 108/101, 149, 143, 102; 312/334.23; 5/58, 646, 507.1, 658, 929

(56) References Cited

U.S. PATENT DOCUMENTS

| | | | | |
|---|---|---|---|---|
| 1,862,237 A | * | 6/1932 | Pepler | 108/49 |
| 3,107,941 A | * | 10/1963 | Davies | 108/49 |
| 5,642,541 A | * | 7/1997 | Corbin | 108/49 |

FOREIGN PATENT DOCUMENTS

FR 798784 A * 5/1936 ................. 108/49

* cited by examiner

Primary Examiner—Peter M. Cuomo
Assistant Examiner—Jerry A. Anderson
(74) Attorney, Agent, or Firm—McAndrews, Held & Malloy, Ltd.; Peter J. Vogel; Michael A. Dellapenna

(57) ABSTRACT

A mount (50) is adapted to be move along a table (20) without disturbing a patient (P) lying on a pad (130) on the table. The mount includes lips (52 and 72) which are joined by a cross member (90) which passes under the table (20).

16 Claims, 4 Drawing Sheets

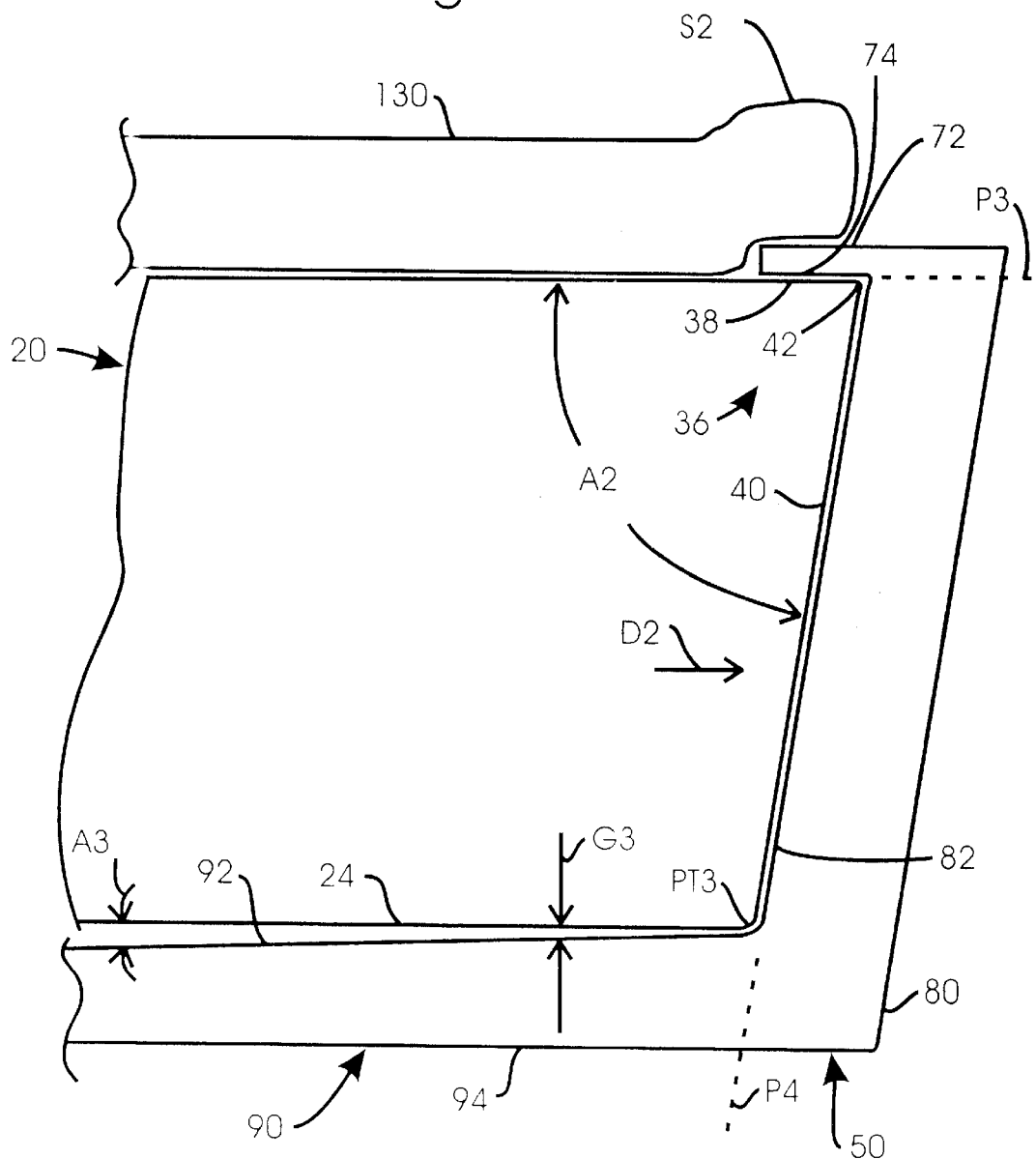

IMAGING TABLE MOUNT

BACKGROUND OF THE INVENTION

This invention relates to mounts for imaging tables, and more particularly relates to mounts capable of accommodating various accessories and peripherals, such as accessory rails, armboards and the like.

Connection of accessories to an imaging table must meet several requirements, and there are a number of desirable features as well. The requirements are onerous because the imaging table is typically constructed of carbon fiber and other composites, making attachment difficult. The requirements are:

The mounts must reduce scatter.

The mounts must be radiolucent.

The mounts must have sufficient strength.

The mounts must be easy to place and remove.

The mounts must be easy to disinfect.

In addition to these requirements, it is desirable to have a method of attachment that also has the following characteristics:

It must be lightweight.

It must have the ability to be placed/removed while a patient is in the imaging position without disturbing the patient, and in a brief period of time It must have the ability to mount without interference to the table comfort pad.

Current mounts are either of the clamping variety, or, are an enclosed, slip-on box. This invention uses an open design that is slip on, but does not have the attendant problems of the box design. A comparative ranking of the various approaches, including the preferred embodiment of the present invention is shown below:

| Requirement/Need | Clamp | Box | Preferred Embodiment |
| --- | --- | --- | --- |
| Mounts must reduce scatter | N | N | F |
| Mounts must be radiolucent | P | N | F |
| Mounts must have sufficient strength | P | F | F |
| Mounts must be easy to place and remove | F | N | F |
| Mounts must be easy to disinfect | P | P | F |
| Lightweight | F | P | F |
| Ability to be placed/removed while a patient is in the imaging position without disturbing the patient, and in a brief period of time | F | N | F |
| Ability to mount without interference to the table comfort pad. | N | N | F |

Legend:
N does not meet;
P partially meets;
F Fully Meets

In summary, the preferred embodiment of the present invention addresses the problems presented by prior known mounts and provides a solution.

BRIEF SUMMARY OF THE INVENTION

The preferred embodiment of the present invention is useful in a medical table comprising an upper surface, a lower surface, a first edge portion and a second edge portion. In such an environment, the preferred embodiment provides a mount for supporting accessories comprising:

a first lip adapted to be carried by the first edge portion;

a second lip adapted to be carried by the second edge portion; and a cross member coupling the first lip with the second lip, whereby the mount is able to move along the table while carried by the first lip and second lip.

By using a mount with the foregoing features, all the advantages described in the table of the background section can be realized. In addition, the preferred embodiment of the invention is highly beneficial to the clinician and technologist who use imaging tables for interventional procedures. Virtually all such procedures have a need for an accessory (or peripheral) device to be attached to the table to successfully complete the procedure. The preferred embodiment is superior to existing designs as described above. In addition, the preferred embodiment improves patient comfort, ease of access to peripherals in the event of an interventional emergency, may reduce radiation exposure to patients and clinicians, and requires less time to clean post-procedure.

BRIEF DESCRIPTION OF THE DRAWINGS

FIG. 5 is a fragmentary cross sectional view of the right hand portion of the mount shown in FIG. 3 installed on the table shown in FIG. 2 and with flange 112 removed.

DETAILED DESCRIPTION OF THE INVENTION

Figure 1:
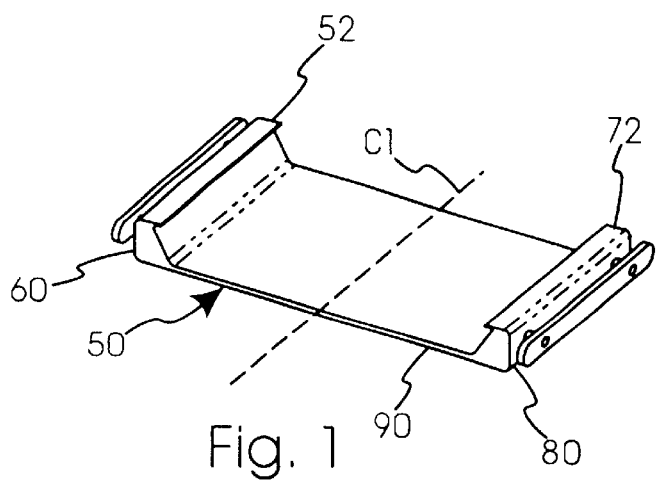
FIG. 1 is a perspective view of a preferred form of mount made in accordance with the invention and employing accessory rails.

Referring to the drawings, a preferred form of the invention is useful in connection with a medical table 20, which may be an interventional imaging table, such as a table used for computed tomography (CT) imaging, magnetic resonance (MR) imaging, ultrasound imaging, x-ray imaging, and the like. Table 20 includes an upper surface 22 and a lower surface 24. An edge portion 26 of table 20 includes a lateral surface 28 and a depending surface 30 which are joined at a junction 32. An edge portion 36 of table 20 includes a lateral surface 38 and a depending surface 40 which are joined at a junction 42.

A mount 50 includes a lip 52 having a lower surface 54 defining a plane P1. Mount 50 also includes a side member 60 having a joining surface 62 defining a plane P2. Plane P1 make an acute angle A1 with plane P2. Lip 52 is carried by lateral surface 28.

Mount 50 also includes a lip 72 having a lower surface 74 defining a plane P3. Mount 50 also includes a side member 80 having a joining surface 82 defining a plane P4. Plane P3 make an acute angle A2 with plane P4 which is equal to angle A1. Plane P1 is coplanar with plane P3. Lip 72 is carried by lateral surface 38.

Mount 50 also includes a cross member 90 which is cantilevered with respect to lower surface 24 of table 20.

Figure 4:
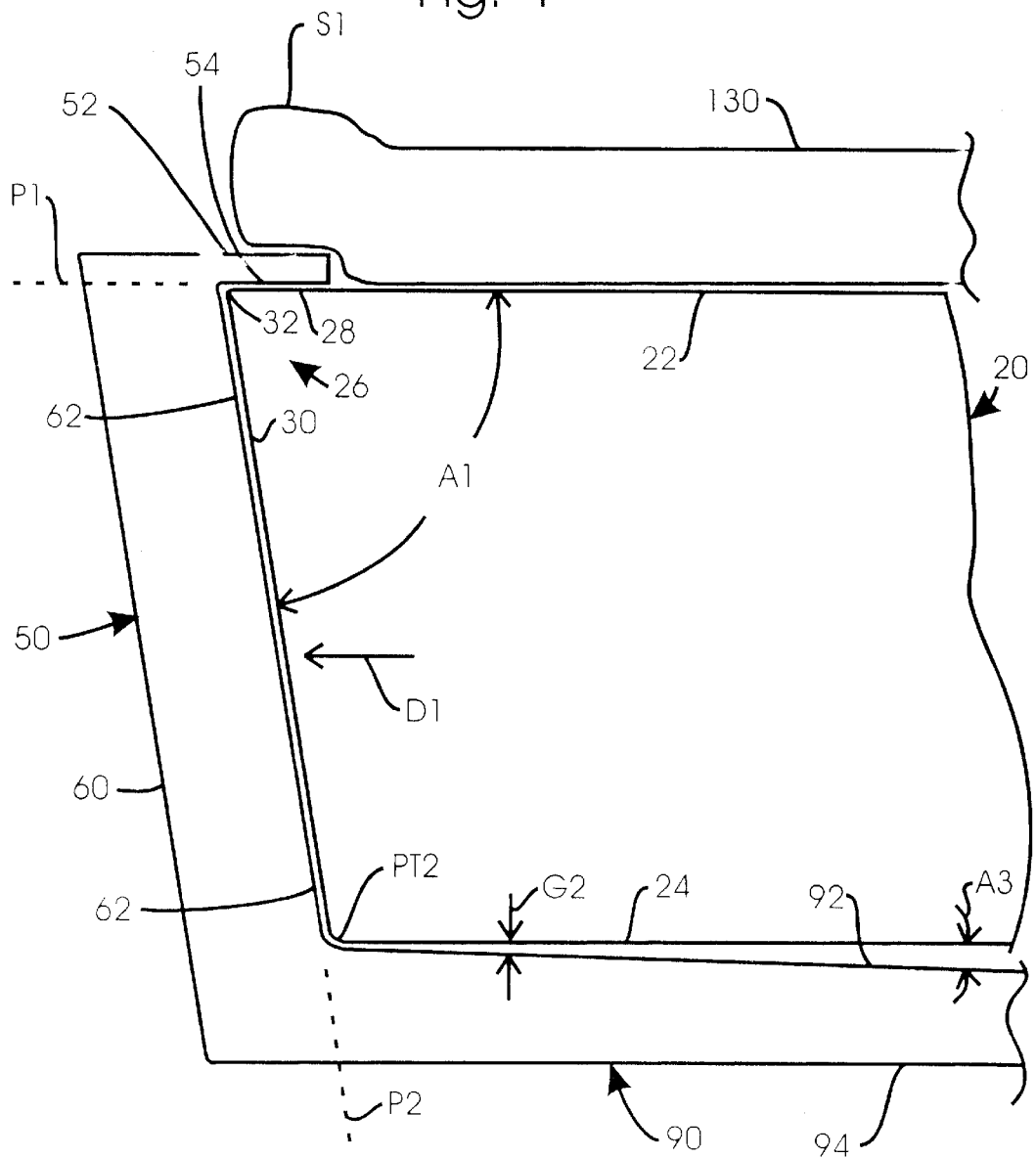
FIG. 4 is a fragmentary cross sectional view of the left hand portion of the mount shown in FIG. 3 installed on the table shown in FIG. 2.

Cross member 90 has an upper surface 92 and a lower surface 94. Surface 92 is separated from surface 24 by a predetermined gap of about 0.25 inch adjacent centerline C1 (FIG. 1). Referring to FIG. 4, at the left hand portion of mount 50, surface 24 is separated from surface 92 by a gap G2 which is less than the predetermined gap. At point PT2, there is nearly a zero clearance between surfaces 24 and 92. Referring to FIG. 5, at the right hand portion of mount 50, surface 24 is separated from surface 92 by a gap G3 which is less than the predetermined gap. At point PT3, there is nearly a zero clearance between surfaces 24 and 92. Surface 92 makes an angle A3 with respect to surface 24.

Figure 3:
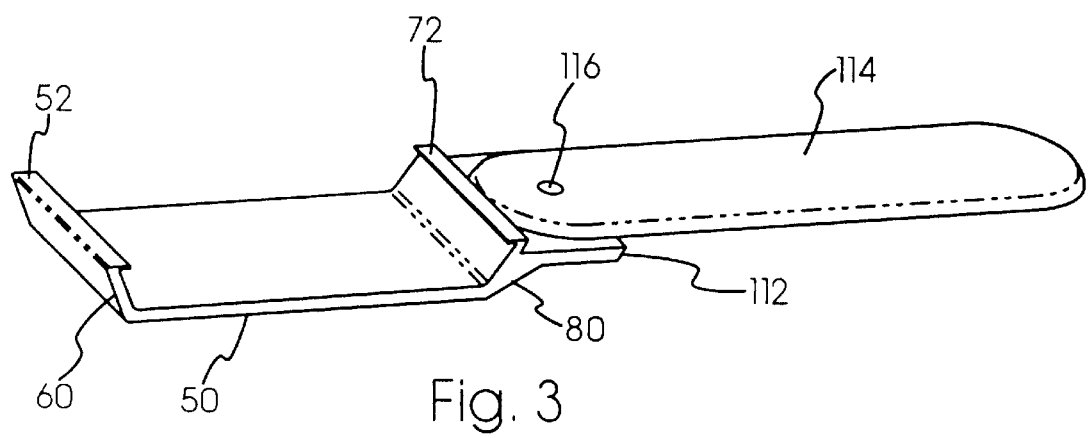
FIG. 3 is perspective view of another form of mount made in accordance with the invention and employing an armboard.

Referring to FIG. 1, members 60 and 80 become thicker as they approach the region where they join cross member 90. Referring to FIG. 3, members 60 and 80 have parallel walls. The objects of the invention may be realized using either shape.

Referring to FIG. 1, mount 50 is joined to an accessory rail 100 by spacers 102 and 104. An accessory rail 106 is joined to mount 50 by spacers 108 and 110.

Referring to FIG. 3, a flange 112 is integrally formed with member 80. An armboard 114 is rotatably mounted on flange 112 with a pivot 116.

Figure 6:
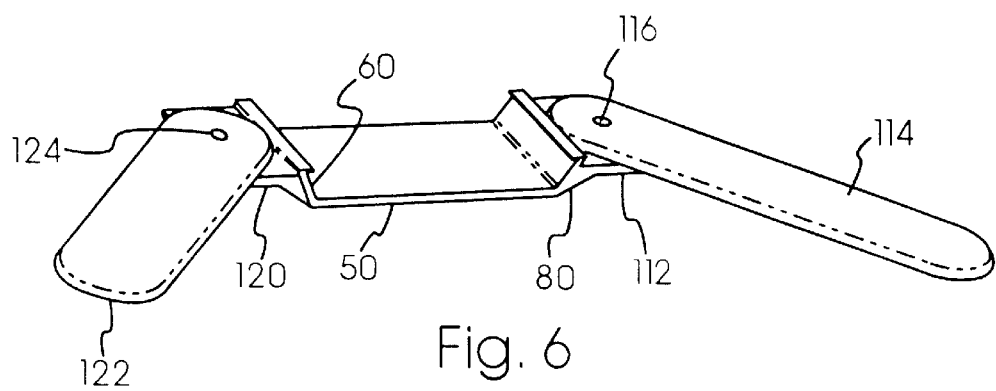
FIG. 6 is a perspective view of another form of mount made in accordance with the invention and employing two armboards.
Figure 2:
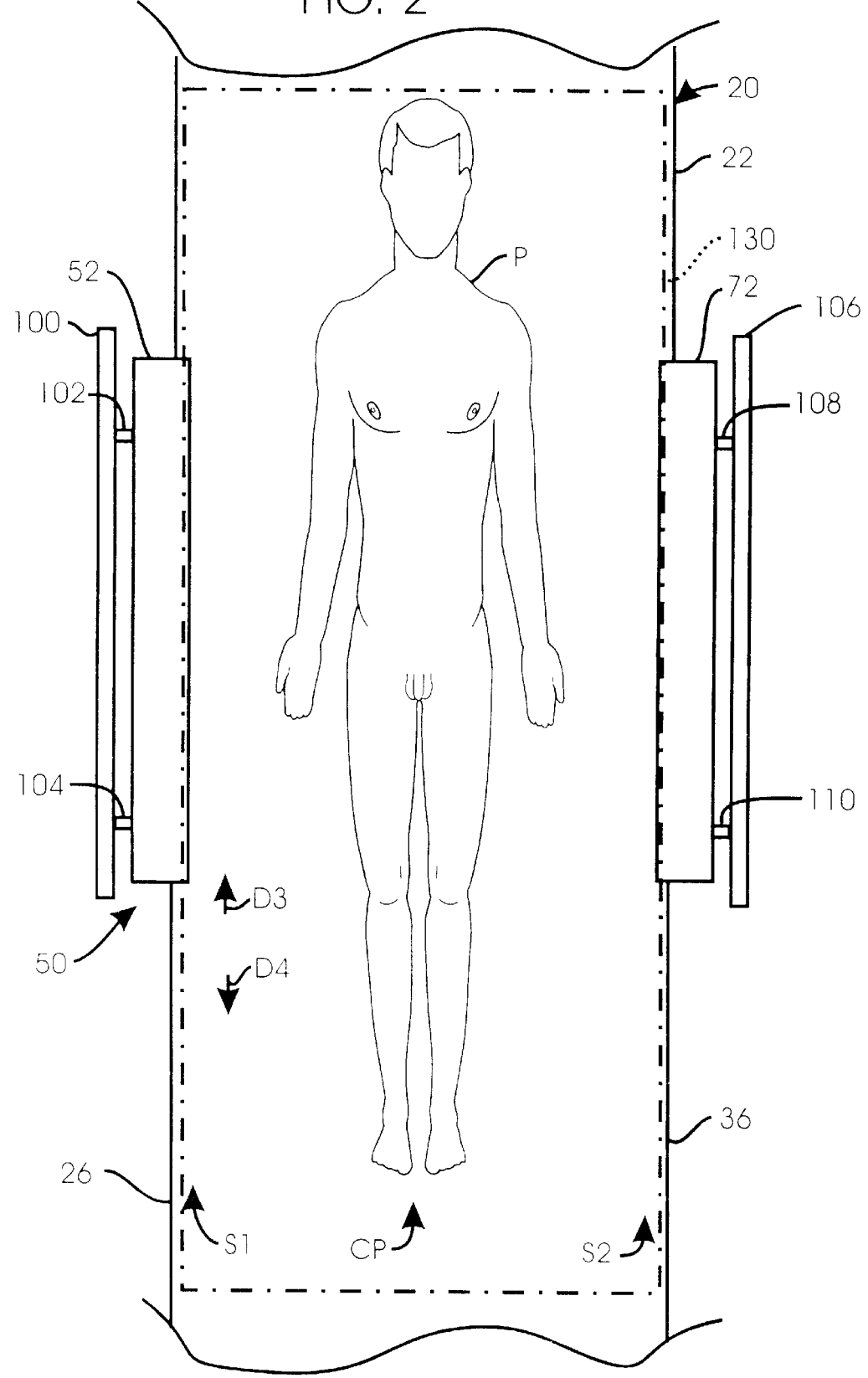
FIG. 2 is a plan view of the mount shown in FIG. 1 mounted on a medical table.

Referring to FIG. 6, a flange 120 is integrally formed with member 60. An armboard 122 is rotatably mounted on flange 120 with a pivot 124.

A pad 130 lies on surface 22 of table 20. A patient P is placed on top of the pad in the center portion CP. Mount 50 is constructed such that it can be slid onto the edge portions 26 and 36 of table 20 while the patient is lying on pad 130 without moving the patient. Lips 52 and 72 slip under the edges of pad 130 as shown in FIGS. 4 and 5. Mount 50 can be moved in either direction D3 or D4 without moving the patient. More specifically, lip 52 slides under side section S1 and lip 72 slides under side section S2. The close spacing between surfaces 30 and 62 prevent motion of mount 50 with respect to table 20 in lateral direction D1. The close spacing between surfaces 40 and 82 prevent motion of mount 50 with respect to table 20 in lateral direction D2. Direction D1 is the opposite of direction D2. The foregoing spacing also enables mount 50 is sustain a torsional load with respect to table 20.

Cross-member 90 is designed to handle mechanical stress. The single cross-member enhances the ability to clean and disinfect mount 50 because there are no small areas where a gloved hand cannot wipe the mount. The open design also allows the device to be placed on table 50 under table pad, but only at the edges where the patient does not place a load on the pad, making the placement/removal easy, even with the patient in place.

Use of an interference joint (e.g., members 60 and 80) with the table shape (e.g., surfaces 30 and 40) provides additional strength. The strength capability is an order of magnitude beyond current designs, making possible new, previously impractical table peripherals (such as on-table injectors). The mount is manufactured from composite materials, providing strength, light weight, increased radiolucency, and reduced X-ray scatter.

Those skilled in the art will recognize that the preferred embodiments may be altered and modified without departing from the true spirit and scope of the invention as defined in the accompanying claims.

What is claimed is:

1. A medical table assembly comprising:
   a medical table comprising:
   an upper surface, a lower surface, a first edge portion comprising a first lateral surface and a first depending surface joined to the first lateral surface at a first junction, the first lateral surface and first depending surface defining a first acute angle, and a second edge portion comprising a second lateral surface and a second depending surface joined to the second lateral surface at a second junction, the second lateral surface and second depending surface defining a second acute angle; and
   a mount for supporting accessories comprising:
   a first lip adapted to be carried by the first lateral surface;
   a second lip adapted to be carried by the second lateral surface; and
   a cross member joined to the first lip by a first member adapted to cooperate with the first depending surface to substantially prevent lateral movement of the mount in a first lateral direction, the first lip and first member defining a third acute angle, the cross member being joined to the second lip by a second member adapted to cooperate with the second depending surface to substantially prevent lateral movement of the mount in a second lateral direction opposite the first direction so that the mount can carry a torsional load, the second lip and second member defining a fourth acute angle, whereby the mount is able to move along the table while carried by the first lip and second lip.

2. An assembly as claimed in claim 1, wherein the first acute angle, second acute angle, third acute angle and fourth acute angle are substantially equal.

3. An assembly, as claimed in claim 1, and further comprising a pad including a center portion for supporting a patient, a first section lying on a first side of the center portion and a second section lying on a second side of the center portion opposite the first side, wherein said first lip is adapted to fit under at least par of the first section and wherein said second lip is adapted to fit under at least part of the second section so that the mount can be placed on the table while the patient is lying on the pad.

4. An assembly as claimed in claim 1, wherein said cross member is cantilevered with respect to said lower surface of said table.

5. An assembly, as claimed in claim 1, and further comprising a first accessory rail coupled to the first member and a second accessory rail coupled to the second member.

6. An assembly, as claimed in claim 1, wherein the cross member defines an upper surface having a central portion displaced from said lower surface of said table by a predetermined gap, having a first side portion separated from said lower surface by a second gap less than the predetermined gap and having a second side portion separated from said lower surface by a second gap less than said predetermined gap.

7. An assembly, as claimed in claim 1, wherein the first lip includes a lower surface defining a first plane and wherein the first member includes a first joining surface adapted to be placed adjacent the first depending surface, said first joining surface defining a second plane making a first acute angle with said first plane.

8. An assembly, as claimed in claim 7, wherein the second lip includes a lower surface defining a third plane and wherein the second member includes a second joining surface adapted to be placed adjacent the second depending surface, said second joining surface defining a fourth plane making a second acute angle with said third plane.

9. An assembly, as claimed in claim 8, wherein the first and second acute angles are equal.

10. An assembly, as claimed in claim 8, wherein the first and third planes are coplanar.

11. An assembly, as claimed in claim 1, and further comprising a first flange adjacent one of the first and second lips.

12. An assembly, as claimed in claim 11, wherein said first flange is adjacent said first lip and wherein said mount further comprising a second flange adjacent said second lip.

13. An assembly, as claimed in claim 12, and further comprising a first armboard movably mounted on the first flange and a second armboard movably mounted on the second flange.

14. An assembly, as claimed in claim 13, wherein the first armboard is pivotally mounted on the first flange and wherein the second armboard is pivotally mounted on the second flange.

15. An assembly, as claimed in claim 11, and further comprising an armboard movably mounted on the first flange.

16. An assembly, as claimed in claim 15, wherein the armboard is pivotally mounted on the first flange.

* * * * *